United States Patent [19]
Laugharn, Jr. et al.

[11] Patent Number: 6,111,096
[45] Date of Patent: Aug. 29, 2000

[54] NUCLEIC ACID ISOLATION AND PURIFICATION

[75] Inventors: James A. Laugharn, Jr., Winchester; Robert A. Hess, Cambridge; Feng Tao, Boston, all of Mass.

[73] Assignee: BBI BioSeq, Inc., West Bridgewater, Mass.

[21] Appl. No.: 08/962,280

[22] Filed: Oct. 31, 1997

[51] Int. Cl.⁷ .................................................. C07H 21/00
[52] U.S. Cl. ........................ 536/25.4; 536/25.41; 422/99; 203/1; 203/2; 203/34; 203/35; 204/193; 204/194; 204/298.25; 204/400; 204/403
[58] Field of Search ................................ 536/25.4, 25.41; 422/99; 203/1, 2, 34, 35; 204/193, 194, 400, 403, 298.25

[56] References Cited

U.S. PATENT DOCUMENTS

| | | | |
|---|---|---|---|
| 3,609,252 | 9/1971 | Broce et al. | 369/134 |
| 5,003,047 | 3/1991 | Yarmush et al. | 530/413 |
| 5,934,766 | 8/1999 | Feigel et al. | 303/119.2 |

*Primary Examiner*—James O. Wilson
*Attorney, Agent, or Firm*—Fish & Richardson P.C.

[57] ABSTRACT

The invention is based on the discovery that hyperbaric, hydrostatic pressure reversibly alters the partitioning of nucleic acids between certain adsorbed and solvated phases relative to partitioning at ambient pressure. The new methods and devices disclosed herein make use of this discovery for highly selective and efficient, low salt isolation and purification of nucleic acids from a broad range of sample types, including forensic samples, blood and other body fluids, and cultured cells.

17 Claims, 6 Drawing Sheets

# NUCLEIC ACID ISOLATION AND PURIFICATION

FIELD OF THE INVENTION

The invention is in the general field of methods and devices for isolating and purifying compounds from mixtures. More specifically, the invention relates to pressure-assisted isolation and purification of nucleic acid molecules.

BACKGROUND OF THE INVENTION

Nucleic acid molecules can be separated from mixtures such as cell lysates or synthetic preparations. Although many methods have been used for this purpose, most are based on a procedure in which the sample is loaded onto a column packed with a solid phase. The negatively charged, anionic phosphate backbone binds to and is thereby effectively immobilized by the solid phase. The solid phase is washed with a low salt solution (e.g., 0.2 M sodium chloride) which flushes away the neutral, cationic, and less highly charged anionic components of the original mixture without disrupting the binding of the nucleic acid molecules to the solid phase.

A high salt buffer solution (e.g., a buffer containing 1 M sodium chloride) is then used to elute the nucleic acid molecules away from the solid phase. The high salt concentration, however, can interfere with mass spectroscopy, electrophoresis, and many downstream enzymatic processes commonly employed in the laboratory or clinic, for example, for diagnostics, forensics, or genomic analysis. It is therefore necessary, in many cases, to remove at least some of the salt from the nucleic acid in an additional, frequently time-consuming step. Desalting can be accomplished by any of several procedures, including ethanol precipitation, dialysis, and purification from glass or silica beads or resin. In some cases it may also be necessary to add nuclease inhibitors to the wash and buffer solutions to prevent degradation of the nucleic acid.

SUMMARY OF THE INVENTION

The invention is based on the discovery that hyperbaric, hydrostatic pressure reversibly alters the partitioning of nucleic acids between certain adsorbed and solvated phases relative to partitioning at ambient pressure. The new methods and devices disclosed herein make use of this discovery for highly selective and efficient, low salt isolation and purification of nucleic acids from a broad range of sample types, including forensic samples, blood and other body fluids, and cultured cells.

In one embodiment, the invention features a device for insertion into a pressure-modulation apparatus. The device includes an electrode array system arranged along two axes; tubes interconnecting the electrodes along the axes, and electrical terminals that contact a current source in the pressure modulation apparatus. The tubes contain a solid phase.

The tubes can be, for example, electrophoretic capillaries or electroosmotic capillaries. Optionally, the electrode array system can be configured on a microchip. The chip can be made, for example, from plastic, glass, silicon, or other metal.

The solid phase can be made from, for example, hydroxyapatite, oligo-dT, silica gel, an anion-exchange resin, or microfabricated silicon.

In another embodiment, the invention features a cartridge for insertion into a high pressure apparatus. The cartridge includes a column adapted to fit into the high pressure apparatus and a solid phase packed in the column. The column can have a capacity of, for example, 10 µl to 5 ml (e.g., 10 µl to 1 ml).

In still another embodiment, the invention features a method for isolating and purifying desired nucleic acid molecules from a sample. The method includes the steps of applying the sample to a solid phase at an initial pressure; washing the sample through the solid phase with a wash solution to flush away non-nucleic acid components that do not bind to the solid phase; modifying the pressure to a level sufficient to disrupt the binding of the desired nucleic acid molecules to the solid phase; and eluting the desired nucleic acid molecules with the wash solution at the modified pressure. The eluted nucleic acid molecules can then be isolated.

The initial pressure can be, for example, ambient pressure and the modified pressure can be an elevated pressure (e.g., 500 to 100,000 psi).

The sample can include cells, in which case the method can also includes the steps of subjecting the sample to a hyperbaric pressure sufficient to lyse the cells prior to applying the sample to the solid phase. The sample can be, for example, a biological fluid, whole blood, serum, cultured cells, living tissue taken from a living or freshly killed organism (e.g., tumor biopsy tissue), primary cells (e.g., stem cells, umbilical cord cells), plant or fungal cells.

The desired nucleic acid molecules can include RNA (e.g., total RNA, messenger RNA (mRNA), or viral RNA) or DNA (e.g., chromosomal or genomic DNA; a vector such as a cosmid, a phage, a plasmid, a yeast artificial chromosome, or an artificial human chromosome; or viral DNA).

In some cases, the increased pressure can be sufficient to elute vector DNA but not high enough to elute chromosomal DNA. Alternatively, the increased pressure can be sufficient to elute RNA but not high enough to elute chromosomal DNA.

In any of the embodiments, the solid phase can be made from hydroxyapatite, oligo-dT, silica gel, an anion-exchange resin, microfabricated silicon, or a pressure-stable medium such as a non-porous resin comprising 1 to 50 µm beads (e.g., glass, quartz, or thermoplastic polymer beads) having a positively charged surface.

The method can optionally include the step of concentrating the nucleic acids between two membranes by electrophoresis, wherein one of the membranes is substantially impermeable to nucleic acids and the second membrane has increased permeability to nucleic acids under applied electrical potential. For example, reagents such as enzymes and PCR primers can be preloaded between the membranes, and the whole chip or apparatus thermally cycled to perform integrated PCR or thermal sequencing.

The method can also include the step of trapping the nucleic acid in a filter or gel by electrophoresis, then, optionally, transferring the nucleic acid from the filter to an analytical device (e.g., a matrix-assisted laser desorption and ionization (MALDI) mass spectrometer).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

An important advantage of the new methods is the potential for use of a single solvent. A single solvent can be used for 1) loading the nucleic acid-containing sample onto the immobilized solid phase, 2) washing non-nucleic acid impurities away from the immobilized nucleic acid, and 3) dissociating the nucleic acid from the solid phase. Single solvent methods can be particularly suitable for purifying high molecular weight nucleic acids. Additionally, if the nucleic acid-containing sample includes cells, the cells can be lysed by hyperbaric pressure in the same solvent as is used for loading, washing, and dissociating.

A single solvent method can be more cost-efficient, can generate less waste, and is generally simpler to implement. Furthermore, the solvent can be the same buffer that is used for a downstream reaction. For example, prepackaged buffers, such as those containing magnesium salts and other cofactors for use in the polymerase chain reaction (PCR), can be used as the loading, washing, and elution buffer in the new methods.

Another advantage of the new methods is the use of solvents that minimize damage to biomolecular constituents. Because pressure can be used to assist the lysis of the cells (if any) in the sample, there is no need for harsh lysis solutions (e.g., phenol/chloroform, guanidinium salts, chaotropic salts) that are often used in vast excess and must subsequently be removed. Since pressure is also used to reduce the affinity of the nucleic acids for the solid phase, high-salt elution solvents are not necessary.

Yet another advantage ensues from the obviation of the need for high-salt elution solvents: the need for desalting procedures is avoided. Desalting is generally necessary if the purified nucleic acids are to be used in further reactions or processes such as PCR, transfection, transformation, electroporation, electrophoresis, mass spectroscopy, quantification with fluorescent dyes, in vitro translation, stringent hybridization, sequencing, genetic engineering, ligation, restriction digestion, genomic mapping, clinical diagnostics, and hybridization with other molecules. In the present methods, the eluted nucleic acid-containing solution does not need to be desalted. The new methods also do not require precipitation in organic solvents, or binding of the nucleic acids to silicon or glass beads for desalting.

The use of low salt buffers also allows the new methods to be compatible with electrophoretic or electroosmotic transfer of materials. Salt can cause excessive heat generation in these processes. Electrophoretic devices are generally inexpensive, can be incorporated into other devices, and can allow isolation of less fragmented nucleic acids (e.g., compared to flow techniques). Electrophoresis can also be used to concentrate nucleic acid samples (i.e., electroconcentration).

Still another advantage of the present methods is that the methods avoid the need for addition of nuclease inhibitors. The majority of proteins are believed to be denatured at pressures lower than 100,000 psi at ambient temperature and neutral pH, whereas nucleic acids can withstand pressures up to about 150,000 psi. Altering pH or temperature can further enhance protein denaturation. Thus, a pressure pulse of, for example, 120,000 psi at pH 4 and 25° C. can effectively inactivate nuclease activity without adversely affecting the desired nucleic acids.

Centrifugation generally is avoided in the processing of the samples for the new methods. This is an advantage in that centrifugation can generate shearing forces and pressure drops that may irreparably damage the integrity of the nucleic acids, thereby decreasing the yield and quality of the isolation. Moreover, the new methods eliminate much of the handling and pipetting of the nucleic acid solutions. As a result, much longer mRNA strands, which may be shorn by routine handling and pipetting, can be isolated intact, thereby facilitating formation of more reliable cDNA libraries, even from mRNA molecules present in low concentration or low copy number. The new methods can give yields of greater than 95% with high purity and speed.

Because all of the steps in the new methods can be carried out in a single solvent, no additional time is required for manipulation of solvents prior to each step. Moreover, the effects of pressure are manifest very rapidly; pressure is transferred through the sample at the speed of sound. As a result, the new methods require only the time that it takes to flush the solvent through the samples; the need to wait for the nucleic acid to precipitate in alcohol, for example, is avoided.

Furthermore, the new methods can be scaled up or down over a large range of sample sizes, from the isolation of the genomic DNA from a single hair follicle to the purification of a plasmid from a megaprep of bacteria. Sample volumes as small as 1 μl or as large as 5 l (e.g., for commercial nucleic acid preparation) can be accommodated by the new methods. Small-scale nucleic acid isolations can be completed within seconds; large-scale isolations may take a few minutes.

Moreover, essentially the same methods can be used for the isolation of small nucleic acids (e.g., less than 50 bp) or large nucleic acids (e.g., larger than 1,000,000 bp). The small molecules elute at lower pressures and lower salt concentrations, and can therefore be independently isolated from samples containing both large and small nucleic acids.

The new methods are also suitable for isolating nucleic acid from a broad range of samples, including, but not limited to, blood, urine, semen, mucal scrapings, sweat, hair, bone, pus, saliva, fecal matter, biopsy tissue, amniotic fluid, synovial fluid, plasma, prokaryotic (e.g., bacteria) or eukaryotic cultures (e.g., plant tissue, yeast, tumor cells), viruses, viroids, and blood-stained materials.

The new methods are also amenable to automation. The new methods require little human intervention; no pipetting, decanting, centrifugation, precipitation, or resuspension of the nucleic acid is generally required. The methods are also highly efficient, and are thus both cost-effective and suitable for high-throughput screening processes (e.g., genetic screening, drug screening). Since the new methods rely on physical processes, little customization is required for different applications.

Other features and advantages of the invention will be apparent from the following detailed description, and from the claims.

DETAILED DESCRIPTION OF THE INVENTION

Methods and devices are described for the highly selective and efficient, low salt isolation and purification of nucleic acids from many types of samples. The invention is based on the observation that pressure can be used to effect the dissociation of nucleic acids from solid phases to which they normally bind tightly (e.g., anion-exchange resins), even in the absence of high salt concentrations.

For example, at 220 MPa (about 32,000 psi), 100% of Lambda DNA ($\lambda$DNA) was eluted off a DEAE column with 250 mM sodium chloride Tris-HCl buffer. At atmospheric pressure (0.1 MPa, or 14 psi), higher salt buffers (e.g., 1 M sodium chloride Tris-HCl buffer) are generally required to elute the DNA away from the DEAE resin. Moreover, plasmid DNA dissociated at lower salt concentrations and lower pressures than $\lambda$DNA. Thus, low molecular weight DNA molecules can be dissociated at lower salt concentrations and lower pressures than higher molecular weight molecules. For sample analysis and other applications, it can be useful to separate nucleic acid fragments by size.

Eukaryotic cells can express cloned genes (i.e., transient and stable heterologous expression), using eukaryotic expression vectors purified by the new methods. To analyze and identify the function of cloned eukaryotic genes, for example, eukaryotic expression plasmids carrying the gene of interest can be obtained in a form suitable for introduction into mammalian cells. It is often necessary to generate a large panel of mutants for structure-function studies of a particular eukaryotic gene. Therefore, the new methods provide a method for rapid and facile analysis.

Isolation of DNA by the new methods can be used for numerous applications including, but not limited to, protein expression and protein structure function studies in eukaryotic cells, Southern blot analysis, in vitro transcription, ligation, and transformation, heterologous protein expression in bacteria or yeast, microinjection studies, PCR, DNA sequencing, viral DNA detection, paternity testing by RFLP analysis, and genetic screening by single-strand conformation polymorphism (SSCP) or non-isotopic RNAse cleavage assay (NIRCA™; Ambion, Austin, Tex.). Similarly, isolation of RNA provides a variety of applications including, but not limited to, genetic analysis, cDNA library construction, microinjection into oocytes, differential display, Northern blot analysis, RNase protection assays, in vitro translation, reverse transcriptase PCR (RT-PCR), and detection of viral RNA (e.g. HIV, hepatitic C, hepatitis A and HTLV-1) in human blood.

General Procedure

In general, a solution containing nucleic acids is introduced onto a solid phase at low pressure (e.g., ambient pressure). The solid phase, to which any nucleic acids present in the solution should now be bound, is then washed with a low salt buffer under ambient conditions. This washing step removes the non-nucleic acid contaminants (e.g., proteins and lipids) from the solid phase, while the nucleic acids remain bound. When the washing is completed, the pressure is increased to a level sufficient to cause the nucleic acids to be freed from the solid phase. While this elevated pressure is maintained, fresh low salt buffer can be used to wash the liberated nucleic acids away from the solid phase and into a collected vessel. These procedures can be fully automated. The recovered DNA is free from high salt and ready for the downstream enzymatic reactions.

Nucleic acids that can be purified by this procedure include chromosomal DNA, viral DNA, plasmid DNA, mitochondrial DNA, a DNA vector, an oligonucleotide, mRNA, mitochondrial RNA, viral RNA, and also mixtures of nucleic acids. The solid phase can be made from any substance that selectively binds to nucleic acids at ambient pressure and has reduced affinity at elevated pressure such as an anion-exchange column, an oligo-dT column, an affinity column (e.g., with immobilized nucleic acid-binding proteins or other molecules), or an electrode coated with absorptive polymers.

In addition to binding nucleic acids, the solid phase can have other functions. For example, the solid phase can absorb the biological samples (e.g., a sponge-type polymer); it can assist in the lysis of the cells, for example by mixing the solid phase material with proteases (e.g., pepsin or trypsin), lipases, or glycosidases (e.g., lysozyme) to digest proteins, lipids, and polysaccharides, respectively; or it can include DNAse for RNA purifications or RNAse for DNA purification. Some solid phases can bind nucleic acids, but only weakly interact with other negatively charged molecules such as some proteins or lipids.

The same solution or different solutions can be used to load the nucleic acid sample onto the solid phase, wash the impurities away, and elute the nucleic acid away from the solid phase. Nonetheless, it is generally most desirable to use a single buffer, both for ease of operation and to reduce waste. Whether the solution acts as a wash buffer or as an elution buffer depends on the pressure. At pressures greater than about 25,000 psi, large (e.g., >5,000 bp) nucleic acids can be eluted in low salt buffers. In addition, at 25,000 psi, small nucleic acids such as those used in the Sanger sequencing method can be eluted at still lower salt concentrations. At ambient pressure, however, it is necessary to use an eluent having a much higher concentration of salt. High salt eluents can interfere with downstream reactions, especially enzymatic reactions used in the manipulation of nucleic acids (e.g., for sequencing or amplification), and are therefore ideally avoided.

As described above, for a low salt buffer to be an effective elution solvent, the pressure in the vicinity of the solid phase must be greatly increased, often to several thousand times ambient pressure. Suitable pressure-modulation apparatuses for generating the requisite pressure are described at pages 4–9 and 29–44 and in FIGS. 1 and 4 of PCT Appln. No. US/96/03232, which was given Ser. No. 08/793,213 in the U.S. National Phase and is now allowed, which are hereby incorporated by reference. A chip or a cartridge containing the solid phase can be inserted into this apparatus and the nucleic acid purification can be carried out within the apparatus. The apparatus can be made in various configurations to accommodate the full range of sample sizes.

Examples of applications of the present method include purification of DNA or RNA from blood, cell-culture (genomics or infectious disease) or tissue (e.g., tumor biopsy) for clinical or research purposes, purification of microbial DNA for genetic or biotechnology research, desalting of DNA, forensic analysis (e.g., purification of DNA from hair, blood, semen, or tissue found at the scene of a crime), and purification of PCR products.

For the purification of nucleic acids from cells (e.g., from cell cultures or tissue), the cells must be lysed prior to the introduction of the sample onto the solid phase. There are many known methods for cell lysis, including chemical methods (e.g., phenol/chloroform extraction, treatment with guanidinium salts, chaotropic salts, detergents such as sodium dodecyl sulfate, or enzymes such as proteinase K) and physical methods (e.g., boiling, French pressing, douncing). Often these methods can be sensitive to variations in time and temperature.

Another suitable method is the use of hyperbaric pressure to cause cell lysis. Hyperbaric lysis can be carried out in the same solvent as will be used as the loading buffer for later introducing the sample onto the solid phase, or can be carried out in a different solvent. Still another suitable method is the use of a chemical agent (e.g., a detergent) in combination with pressure. For example, a small amount of a chaotropic salt can be used to prime the cells for lysis; after the cells have been treated with the chaotropic agent, they can be lysed at lower pressure.

More gentle lysis procedures can be especially preferable for isolating single-strand nucleic acid molecules (e.g., RNA), or if the nucleic acid to be isolated is of high molecular weight, since single strands are easier to shear and longer nucleic acid strands are statistically more likely to be shorn during lysis.

Most proteins (e.g., nucleases) are inhibited by pressure. A 120,000 psi pulse, for example, can irreversibly denature the nucleases in a sample. It is important, especially in attempted isolations of RNA, to denature nucleases such as RNAse to prevent degradation of the desired nucleic acids during the isolation process. Pressure can be used here in place of chemical inhibitors. In some cases, nuclease denaturation and cell lysis can be accomplished simultaneously.

In some cases, all of the steps of nucleic acid purification, including lysis, binding, elution, and isolation, can be automated. Additionally, the pressure can be ramped to allow elution of progressively larger nucleic acids, thereby facilitating the isolation of specific sizes of molecules. A pressure gradient (i.e., either stepped or continuous) can also be set up within the devices. A pressure gradient can be used, for example, to fractionate samples. Fractionation can be used to purify specific fragments from a partially degraded sample or a highly diverse sample (e.g., a cDNA library).

Cartridges

Figure 1:
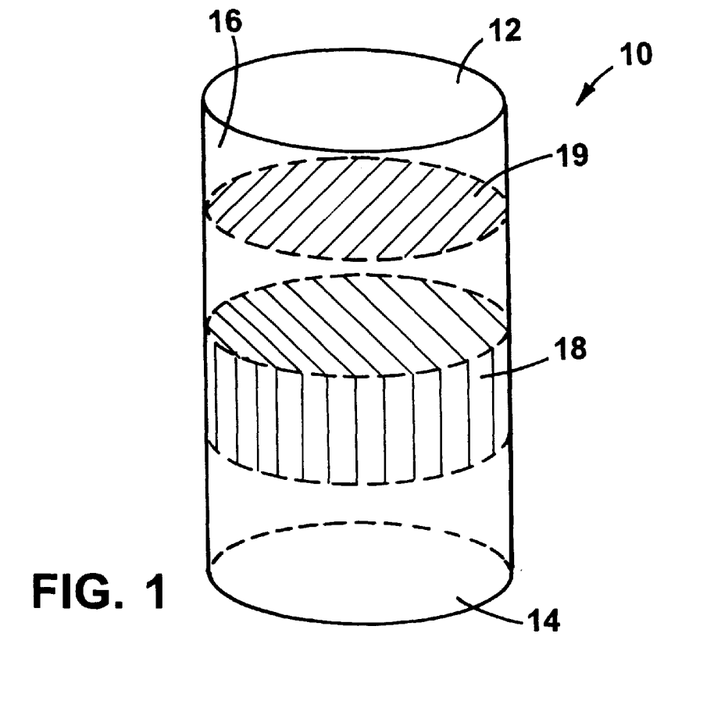
FIG. 1 is a drawing of a resin-filled cartridge for use in a pressure-modulation apparatus.

One design for an isolation device is shown in FIG. 1. This device is a cartridge 10 made of metal (e.g., titanium, stainless steel, or aluminum), plastic (e.g., a thermoplastic such as polypropylene or polytetrafluoroethylene), glass, quartz, stone (e.g., sapphire), or a ceramic, adapted to fit into a pressure-modulation apparatus such as those described at pages 4–9 and 29–44 and in FIGS. 1 and 4 of PCT Appln. No. US/96/03232, which was given Ser. No. 08/793,213 in the U.S. National Phase and is now allowed.

The cartridge is generally formed in the shape of a tubular column, although other designs can be used. Regardless of the shape, the cartridge usually has two openings 12 and 14, one 12 to allow fluid to enter and another 14 to allow the fluid to exit. Between the two openings, but within a channel 16 common to the openings, a solid phase material 18 is packed. The solid phase can be any of a multitude of nucleic acid-binding materials, including silica gel, anion-exchange resin (e.g., DEAE), tethered nucleotides or nucleic acids (e.g., oligo-dT and complementary oligonucleotide probes), tethered proteins or peptides, polymers, DNA-binding molecules (e.g., ethidium, acridinium), or other small molecules (e.g., sugars, benzodiazepines, drugs).

The cartridge can be designed such that the openings are in direct fluid contact with the reaction chamber of the pressure-modulation apparatus, or can be designed as a closed system with valves and pistons that can open and close to regulate the pressure and the fluid flow within the cartridge. The valves and pistons in this embodiment can be controlled either electronically or mechanically.

Cartridges designed for use with samples derived from lysed whole cells can optionally include a micro-porous filter or membrane 19 positioned to filter off any remaining cell debris prior to introduction of the sample onto the solid phase. This filter may be larger in cross-sectional area than the resin chamber to prevent pressure gradients.

The volume of the cartridges can vary widely. For example, the cartridge can have an internal volume of 10 $\mu$l or 10 ml. Preferably, the internal volume is 100 $\mu$l to 1 ml. Typically, the solid phase occupies about half of the internal volume of the cartridge, although some cartridges can be filled to nearly to their full capacity while others may be filled just one tenth of the way. In some cases, the cartridges can be reused.

Although the cartridge size is ideally matched to the size of the sample, the cartridges can frequently be loaded with samples whose volumes exceed the cartridge capacity 2-, 10-, or even 100-fold, especially if the nucleic acid concentration in the sample is relatively low. One limiting criterion is the ratio of free nucleic acid-binding sites on the solid phase to the number of nucleic acid molecules; if the amount of nucleic acid exceeds the number of binding sites, then some of the nucleic acid will pass through the cartridge without being bound. Furthermore, if the solid phase material is very dense, the capacity can be further limited since the bound nucleic acid molecules can further impede the flow of additional fluid through the cartridge.

In the operation of the cartridges, the sample is dissolved or suspended in a low-salt buffer solution and introduced at opening 12. The cartridge 10 is placed in the pressure-modulation apparatus. A low pressure flow of buffer solution is used to force the sample through the membrane 19 and through the solid phase 18. Nucleic acids in the sample bind to the solid phase; the flow-through continues through the solid phase and emerges from opening 14. In some cases, the flow-through is taken up by a sample output tube leading to an input on a detection device (e.g., a UV-vis spectrophotometer). The low pressure flow of the buffer solution is continued until the detection device shows that no additional residues are washed away. The flow-through is discarded.

The pressure is then increased to 500 to 100,000 psi, causing the nucleic acid to be released from the solid phase. More of the buffer solution is introduced through opening 12, and the nucleic acid-containing flow-through that emerges from opening 14 is collected. This flow-through can also be fed into a detection device and analyzed, and the flow continued until the nucleic acid detected in the flow-through falls below a set threshold level.

The cartridges can also include multiple compartments. For example, the individual compartments can contain different solid phase materials (e.g., ion-exchange resin, silica gel, tethered oligonucleotides). Reactions can be carried out within the cartridges.

For instance, a cartridge of the present invention can be used as a PCR reaction vessel, if placed within a thermal cycling apparatus after the solid phase has been washed to remove non-nucleic acid impurities and the nucleic acid has been eluted from the solid phase into, for example, a second compartment in the cartridge.

A multi-compartment cartridge can also be used to concentrate nucleic acids. For example, fluids can be moved hydrodynamically or electrically, or both. In one example, DNA from a large sample can be concentrated hydrodynamically onto a resin, small molecule impurities can be washed away, then the DNA can be electrically electrophoresed into a downstream cartridge. This process is termed electroconcentration.

In another two-part cartridge, nucleic acids are eluted from a first compartment (e.g., containing an anion-exchange resin), using pressure, and concentrated in a second compartment (e.g., containing silica gel) that requires different conditions for elution. Thus, concentrated nucleic acids can be isolated from eve dilute samples containing many impurities. Alternatively, the eluted sample can be automatically transferred to another device (e.g., a disk, a pad, a bead, or a detection device).

Chips

Figure 2:
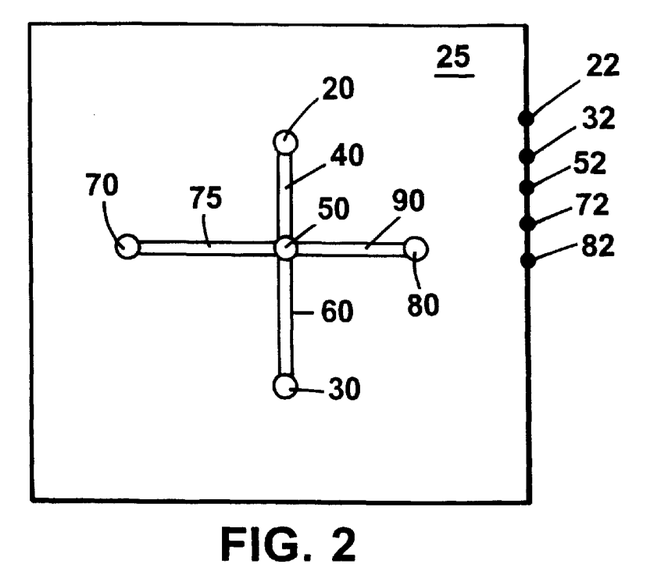
FIG. 2 is a drawing of a five electrode chip for use in a pressure-modulation apparatus.
Figure 3:
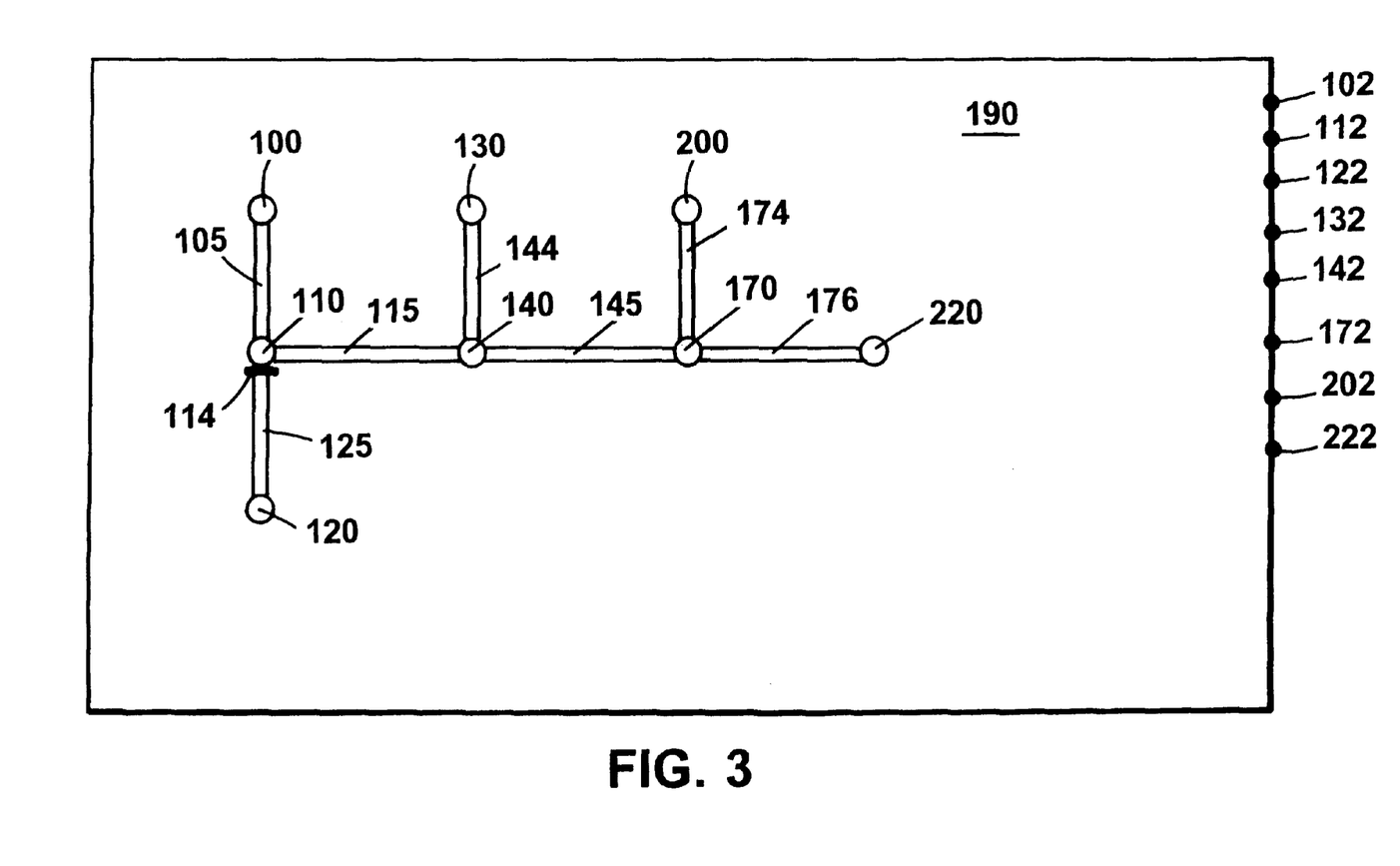
FIG. 3 is a drawing of an eight electrode chip for use in a pressure-modulation apparatus.

An alternative design for an isolation device is shown in FIGS. 2 and 3. These devices are in the form of a chip, with an electrode array aligned along at least two axes. The individual electrodes are coated with a solid phase material. In some cases, all of the electrodes are coated with the same material; in other cases, the coatings differ from electrode to electrode or form a coating gradient along a capillary connecting two or more electrodes. The chips can optionally be interfaced with an analytical device such as a mass spectrometer or a capillary electrophoresis device.

Although the design of the chips can vary widely, the operation of the chips is similar irrespective of the design. In one of the simplest designs (FIG. 2), electrodes 20, 30, 50, 70, and 80 are electrically connected to contact points 22, 32, 52, 72, and 82, respectively. A sample containing chromosomal DNA to be isolated is introduced at electrode 20 at ambient pressure. In addition to the nucleic acids to be isolated, the sample can include salt (e.g., 50 to 350 mM sodium chloride) and various impurities. Electrode 20 is coated with a material that absorbs the sample.

The chip 25 is placed within the sample chamber of a pressure-modulation apparatus (e.g., the apparatus described in U.S. Ser. No. 08/903,615) adapted to supply a switchable electrical voltage at the contact points 22, 32, 52, 72, and 82. A voltage potential is supplied between electrodes 20 and 30 (i.e., electrode 20 is the anode and electrode 30 is the cathode) while the system is at ambient pressure. The potential causes the sample to flow through capillary 40, which is filled with a size-exclusion filtration material (e.g., 0.5% agarose) that retains large cellular debris but allows nucleic acids, proteins, lipids, and other small cellular components to pass through.

The flow-through then passes through to electrode 50, which is coated with an anion-exchange resin. Nucleic acids in the molecule are trapped at electrode 50, while the remaining components in the flow-through continue through the aqueous solution in capillary 60, and ultimately, to electrode 30. Electrode 30 includes a reservoir that traps the impurities that reach it. The voltage potential between electrodes 20 and 30 is then discontinued.

The pressure in the system is increased to a moderately elevated level (e.g., 500 to 10,000 psi). A voltage potential is set up between electrodes 50 (anode) and 80 (cathode). The moderate pressure causes the smallest nucleic acids (e.g., less than 5,000 bp) to dissociate from the anion-exchange resin at electrode 50, and the potential causes the nucleic acid to migrate through the liquid phase in capillary 90 and finally into electrode 80, which includes a reservoir. The potential is discontinued.

The pressure in the system is increased to a more elevated level (e.g., 12,000 to 100,000 psi). A voltage potential is set up between electrodes 50 (anode) and 70 (cathode). The high pressure causes the remaining nucleic acids to dissociate from the anion-exchange resin at electrode 50, and the potential causes the nucleic acid to migrate through the liquid phase in capillary 75 and finally into electrode 70, which includes a reservoir. The potential is discontinued, the pressure is lowered to ambient pressure, the chip is removed from the pressure-modulation apparatus, and the large nucleic acid fraction, including the chromosomal DNA, can be removed from electrode 70.

In another design (FIG. 3), electrodes 100, 110, 120, 130, 140, 170, 200, and 220 are electrically connected to contact points 102, 112, 122, 132, 142, 172, 202, and 222, respectively. A whole blood sample is introduced at electrode 100 at ambient pressure. Electrode 100 is coated with a wicking material that absorbs the sample.

The chip 190 is placed within the sample chamber of a pressure-modulation apparatus adapted to supply a switchable electrical voltage at the contact points 102, 112, 122, 132, 142, 172, 202, and 222. A voltage potential is supplied between electrodes 100 (anode) and 120 (cathode) while the system is at ambient pressure. The potential causes the sample to flow through liquid-filled capillaries 105 and 125 and electrode 110. At the junction between electrode 110 and capillary 125, a filter 114 prevents white blood cells to pass. Thus, the white blood cells become trapped at electrode 110, while red blood cells continue to migrate to electrode 120.

The pressure is increased momentarily (e.g., 80,000 to 120,000 psi), lysing the cells at electrodes 110 and 120, and inactivating any nucleases present in the cell lysates. The pressure is then restored to ambient pressure. A potential is then provided between electrodes 110 (anode) and 220 (cathode). Capillary 115 contains a size-exclusion material or an ion-exchange material, for example, that can retain large cellular debris but allow nucleic acids, proteins, lipids, and other small cellular components to pass through.

The flow-through then passes through to electrode 140, which is coated with oligo-dT, and through to electrode 170, which is coated with an anion-exchange resin. RNA in the white blood cell lysate is trapped at electrode 140 and DNA in the white blood cell lysate is trapped at electrode 170, while the remaining components in the flow-through continue through the aqueous solution in capillary 176 and ultimately to electrode 220. Electrode 220 includes a reservoir that traps the impurities that reach it. The potential is then discontinued.

A potential is supplied between electrodes 140 (anode) and 130 (cathode). The potential causes the RNA to dissociate from the solid phase at electrode 140, migrate through the liquid phase in capillary 144, and finally to electrode 130, where a reservoir traps the RNA. The potential is discontinued.

The pressure in the system is then increased to an elevated level (e.g., 20,000 to 100,000 psi), and a potential is supplied between electrodes 170 (anode) and 200 (cathode). The pressure causes the DNA to dissociate from the solid phase at electrode 170, and the potential causes the nucleic acid to migrate through the liquid phase in capillary 174, and finally to electrode 200, where a reservoir traps the DNA. The potential is discontinued, the chip is removed from the pressure-modulation apparatus, the purified white blood cell RNA can be removed from electrode 130, and the purified white blood cell DNA can be removed from electrode 200.

There may be multiple versions of this device or consumables for use with the device that are optimized for various applications and sample sizes. For instance, a miniature version can be highly parallel and/or interface into a downstream biochip. Examples of sample sizes include 10 µl, 100 µl, 1 ml and 10 ml.

The chips can be made from metal (e.g., silicon), plastic (e.g., polypropylene or polytetrafluoroethylene), glass, or ceramic. The contact points and electrodes can be made, for example, from gold, silver, copper, or iron.

The chips can be designed such that the fluids in the capillaries are in direct fluid contact with the reaction chamber of the pressure-modulation apparatus. More preferably, the chips can be designed as a closed system with a diaphragm (FIG. 4), a piston (FIG. 5), or a hydrophobic valve (FIG. 6), which relays the pressure from the reaction chamber to the capillaries and electrodes.

Figure 4A:
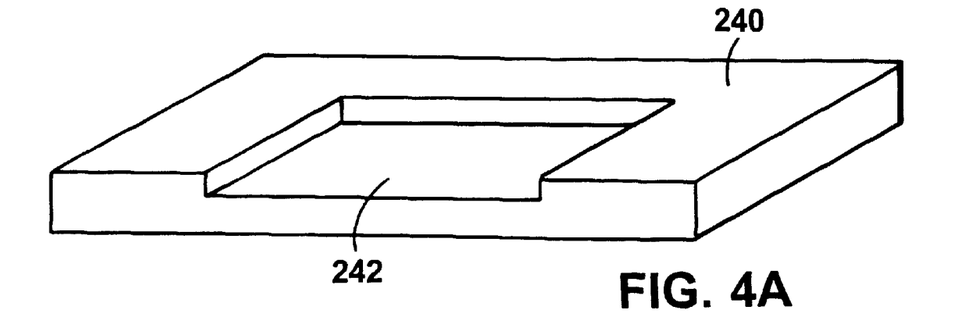
FIG. 4A is a cut-away perspective view of a chip of the invention.
Figure 4B:
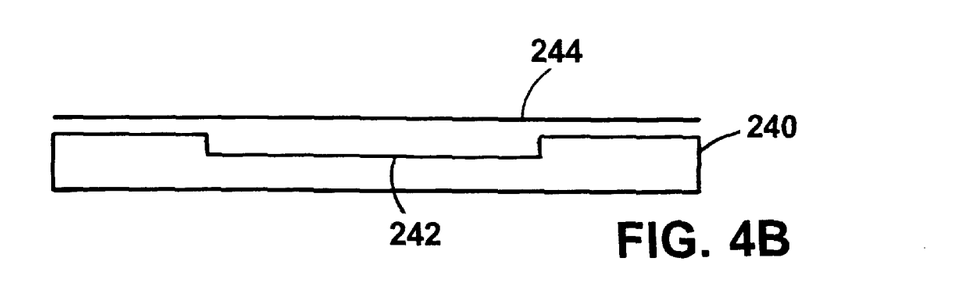
FIG. 4B is an exploded side view of a chip of the invention that includes a diaphragm for relaying pressure.
Figure 4C:
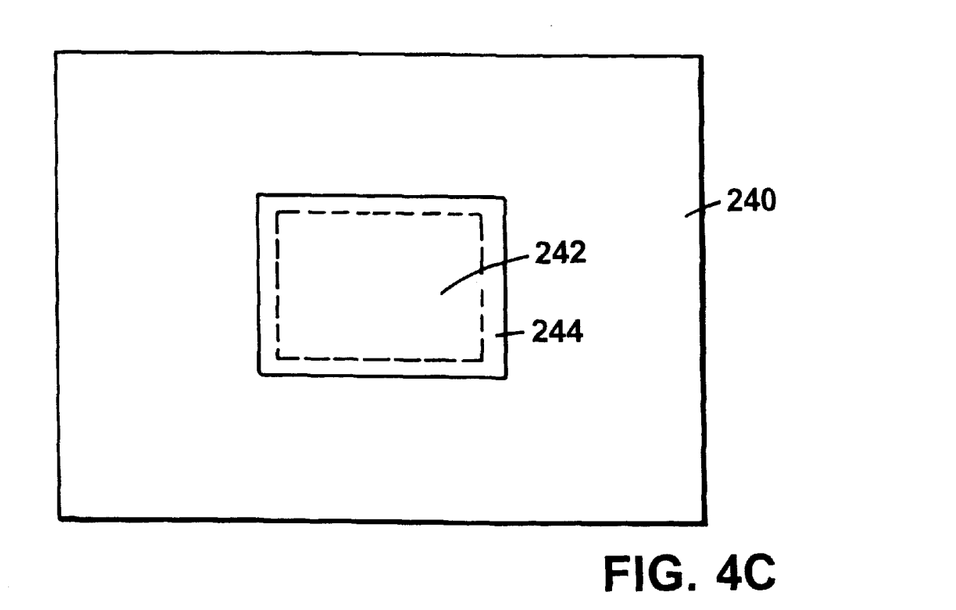
FIG. 4C is a top view of a chip of the invention that includes a diaphragm for relaying pressure.

As shown in FIGS. 4A to 4C, the chip 240 can include a recessed area 242, in which the electrode array is situated. A flexible, elastic membrane 244 spans the recessed area 242, to form a diaphragm. One or both surfaces of the membrane can be flexible. The membrane transmits external pressure to the electrode array, while simultaneously providing a hermetic seal that prevents fluids from being transferred.

Figure 5A:
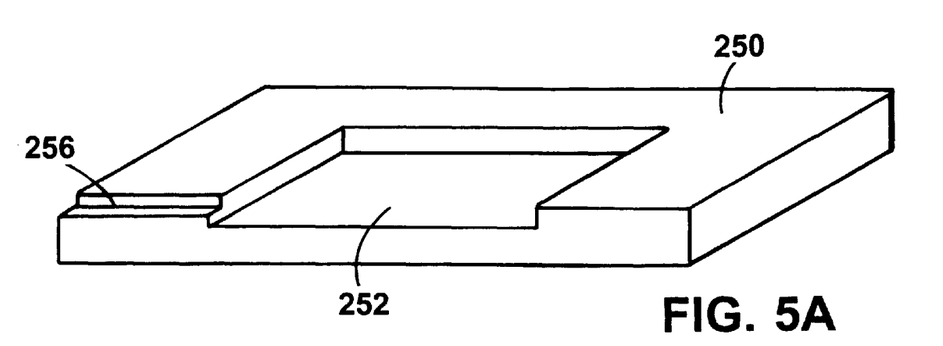
FIG. 5A is a cut-away perspective view of a chip of the invention.
Figure 5B:
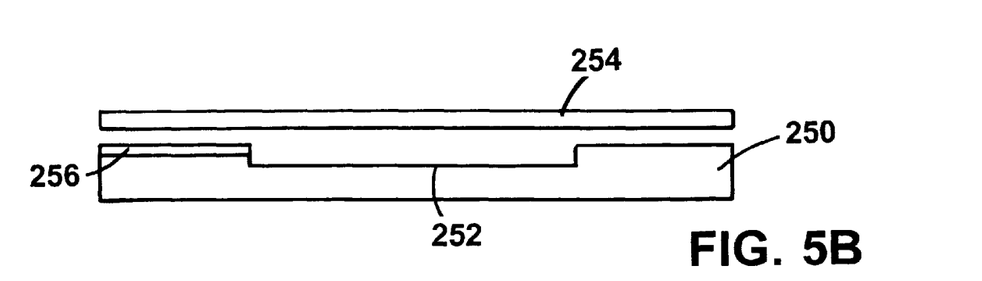
FIG. 5B is an exploded side view of a chip of the invention that includes a hydrophobic valve for relaying pressure.
Figure 5C:
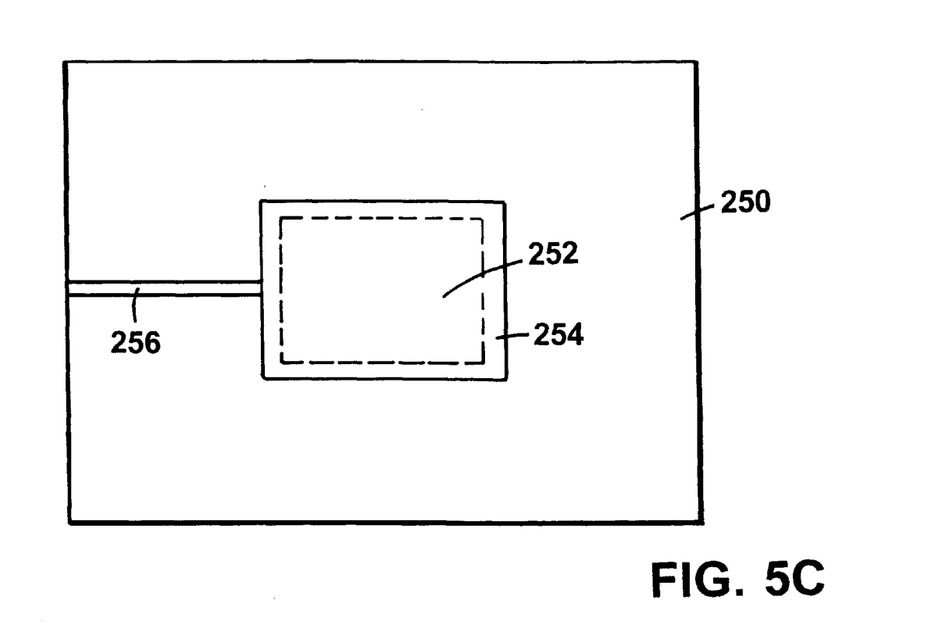
FIG. 5C is a top view of a chip of the invention that includes a hydrophobic valve for relaying pressure.

The chip 250 shown in FIGS. 5A to 5C also includes a recessed area 252, in which the electrode array is situated. A solid lid 254 is placed over the recessed area. A channel 256 is drilled through one side of the chip, leading into the recessed area 252. The wall of the channel 256 is precoated with a hydrophobic material, such that water and other fluids are unable to traverse the length of the channel 256 under ambient conditions. As the pressure is increased, however, the fluids overcome the hydrophobic interactions and pass through the channel 256, thereby modulating the pressure within the recessed area 252.

Figure 6A:
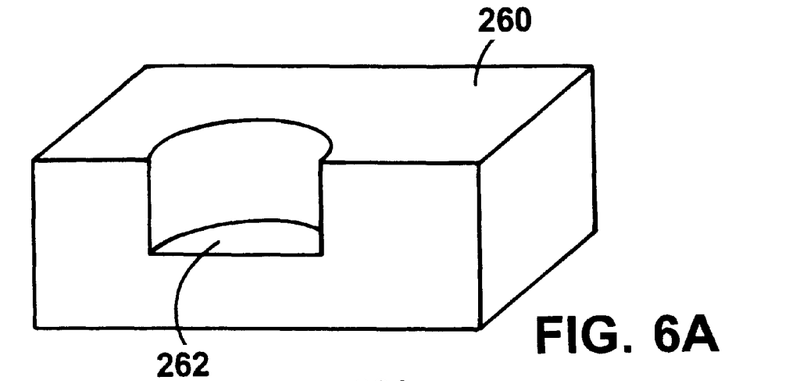
FIG. 6A is a cut-away perspective view of a chip of the invention.
Figure 6B:
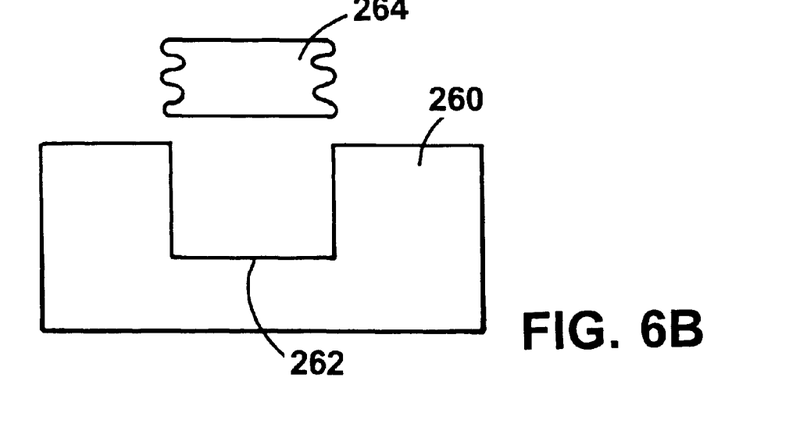
FIG. 6B is an exploded side view of a chip of the invention that includes a compressible piston for relaying pressure.
Figure 6C:
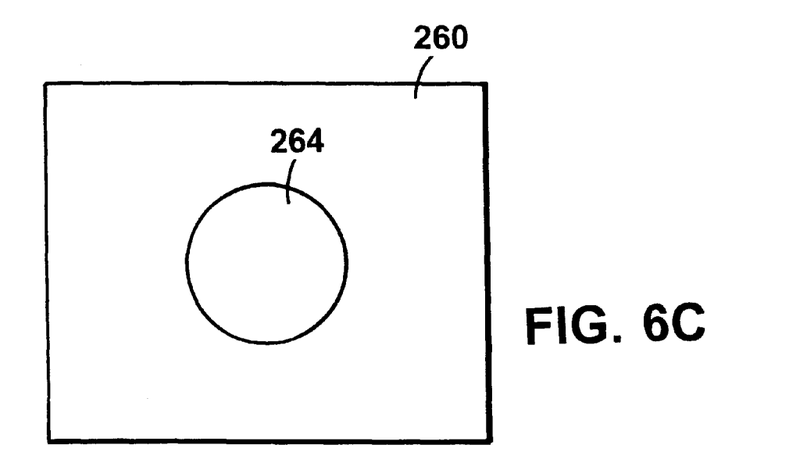
FIG. 6C is a top view of a chip of the invention that includes a compressible piston for relaying pressure.

In a third design, shown in FIGS. 6A to 6C, a chip 260 includes a recessed area 262, in which the electrode array is situated. A compressible, elastomeric piston 264 is mounted in the recessed area 262. When the pressure in the reaction chamber is increased, the piston 264 becomes compressed, thereby increasing the pressure at the electrode array without allowing fluid transfer between the reaction chamber and the electrode array.

Disposable Two-Syringe Device

In another embodiment of the invention, the sample is placed into a first (loading) syringe having a DEAE resin cartridge attached at the narrow end. This system must have a very small resin chamber so that high pressures can be generated and the materials must be able to withstand the high pressures. The plunger is slowly depressed, so as not to create a significant pressure gradient. As the sample is loaded onto the resin, the waste is discarded. Low salt (e.g., 10 to 300 mM) buffer is placed in the syringe. The buffer can contain magnesium and other cofactors necessary for downstream enzymatic techniques. A measured quantity (e.g., 100 µl to 10 ml) of the buffer is used to wash the resin to remove non-DNA contaminants.

A second (collection) syringe is added to the first. The resistance of the plunger of the second syringe is adjusted such that the pressure needed to move the loading syringe causes the dissociation of the nucleic acid from the resin. The resisting force exerted by the collection syringe can be adjusted by means of low-angle threads in the syringe and piston. The angle of the threads can be adjusted to change the pressure. For applications where consistency of yield and purity are crucial, the pressurizing step can be carried out by, or with the aid of, a machine that maintains a consistent pressure and flow rate. For non-critical applications, this step can be done manually.

Another version of this system would use a device which applied an equal force to two opposing pistons and (with much less force) moved the two syringes simultaneously to achieve a flow. In another version, two pistons supply force, with a small pressure differential between them. This system can be immersed in a pressurizing medium (such as water) so as to avoid the use of pressure resistant materials and small resin capacity in the disposable component.

The following illustrative examples are not intended to limit the scope of the invention.

EXAMPLE 1

DNA Isolation and Purification in an Anion-Exchange Cartridge

DNA samples were separated using a Qiagen DEAE anion-exchange resin (Qiagen, Inc., Santa Clarita, Calif.) at ambient and elevated pressures. The DEAE resin was packed into a 9 mm×4 mm I.D. (5 mm O.D.) stainless steel 'half-column' capped with Teflon® frits with a 2 µm pore size (Valco Instrument Company, Inc., Houston, Tex.). Two half-columns, one containing resin and the other acting as a spacer and devoid of resin, were placed into a column holder. The column holder was a metal tube with an inner diameter of 5 mm and syringe fittings at the ends to allow fluid to flow through the columns.

Pressure elution of DNA was performed using a pressure apparatus as described at pages 29 et seq. of PCT Appln. No. US/96/03232, which was given Ser. No. 08/793,213 in the U.S. National Phase and is now allowed, controlled by a microcomputer with LABVIEW™ software (National Instruments, Austin, Tex.). The columns were inserted into a pressure chamber adapted to receive the columns. Liquid was injected and removed from the chamber using a series of pneumatic valves and pistons as described in the '232 application, allowing for elution of DNA from the column while maintaining elevated pressure within the column.

The DEAE column was initially washed with 1 ml high salt elution buffer (1.25 M sodium chloride; 50 mM Tris-HCl, pH 8.5; 15% ethanol) and equilibrated with 1 ml equilibration buffer (750 mM sodium chloride; 50 mM MOPS, pH 7.0; 15% ethanol; 0.15% Triton X-100). Approximately 300 µl of 21 µg/mL DNA in loading buffer (1 M potassium acetate; 33 mM NaCl; 33 mM Tris-HCl, pH 5; 8 mM EDTA), was injected into the packed column over five minutes, in four 1 minute intervals. 1 ml of MO washing buffer (containing 1 M NaCl; 50 mM MOPS, pH 7.0; 15% ethanol) was then injected through the holder to remove any remaining contaminants, followed by 200 μl of elution buffer to displace the MO washing buffer prior to elution either at atmospheric or elevated pressures. Elution buffers used during the DNA elution step contained 50 mM Tris-HCl, pH 8.5, and various concentrations of sodium chloride.

Four consecutive 300 μl elution fractions were collected during each experiment. Each fraction was collected over a three minute interval, in which a 100 μl pressure wash step with the elution buffer was performed each minute. Experiments at atmospheric pressure were performed with identical elution steps, using a syringe to deliver the elution salt solutions through the column holder.

DNA in the collected samples was quantified using Oli-Green DNA binding dye (Molecular Probes, Eugene, Oreg.). To reduce the background signal and increase sensitivity, DNA assay solutions were first diluted 20–200 fold with TE buffer (10 mM Tris-HCl, 1 mM EDTA, pH 7.5) and then complexed with the OliGreen dye (20,000:1 DNA:dye in volume). Fluorescence emission intensity ($\lambda_{em}$=520 nm, $\lambda_{ex}$=480 nm) of the DNA/OliGreen solution was measured with an ISS PCI spectrofluorometer (ISS, Inc., Champaign, Ill.), without background subtractions. Quantitation of DNA was made by comparing the measured intensity with calibration curves obtained from known DNA concentrations. Recovery of DNA in the elution fractions was calculated by dividing total DNA in the elution fractions with the total DNA bound in the column, (i.e., total DNA loaded minus DNA in flow-through and MO washing solutions).

At elevated pressures, λDNA (Worthington Biochemical Company, Freehold, N.J.) was released from the DEAE resin with a buffer of lower salt concentration, as shown in Table 1. The percentages given in the table are percent recoveries, and numbers in parentheses after the percentages are the number of times the corresponding experiments were carried out. The error range was calculated to be approximately 5% based on the duplicated data.

TABLE 1

| [NaCl] (M) in Tris Buffer | Pressure (MPa) | | | |
|---|---|---|---|---|
| | 0.1 | 90 | 170 | 220 |
| 0.10 | trace (1) | | trace (1) | 40% (1) |
| 0.25 | trace (2) | | 20% (3) | 100% (1) |
| 0.40 | | | 25% (1) | |
| 0.50 | trace (2) | 15% (1) | 70% (2) | 60% (1) |
| 0.75 | trace (2) | 15% (1) | 100% (2) | trace (1) |
| 1.00 | 100% (1) | | 100% (1) | |

Table 1 shows a correlation: the higher the pressure, the lower the salt concentration needed for dissociation. At 0.1 MPa (i.e., atmospheric pressure), 1 M sodium chloride was required for more than just a trace amount (i.e., less than 10%) of DNA to be eluted. At 90 MPa (about 12,500 psi), the DNA showed a slightly increased tendency to dissociate; at 170 MPa (about 24,000 psi), 70% of the λDNA was dissociated with 0.50 M NaCl. 100% of the λDNA dissociated with 0.25 M NaCl at 220 MPa (about 32,000 psi). Interestingly, less of the DNA eluted at this pressure when the salt concentration was raised, possibly due to electrostriction or salvation effects.

A follow-up experiment included three different sizes of DNA. Human cell extract high molecular weight DNA K562 (number of bp is unknown; Pharmacia Biotech, Inc., Piscataway, N.J.) and λDNA (~48.4 kb) behaved similarly. Both yielded a 25% recovery with 0.40 M NaCl Tris-HCl buffer at 170 MPa. On the other hand, 100% recovery of the plasmid pKK223-3 (about 4.6 kb DNA) was observed under the same conditions.

Figure 7:
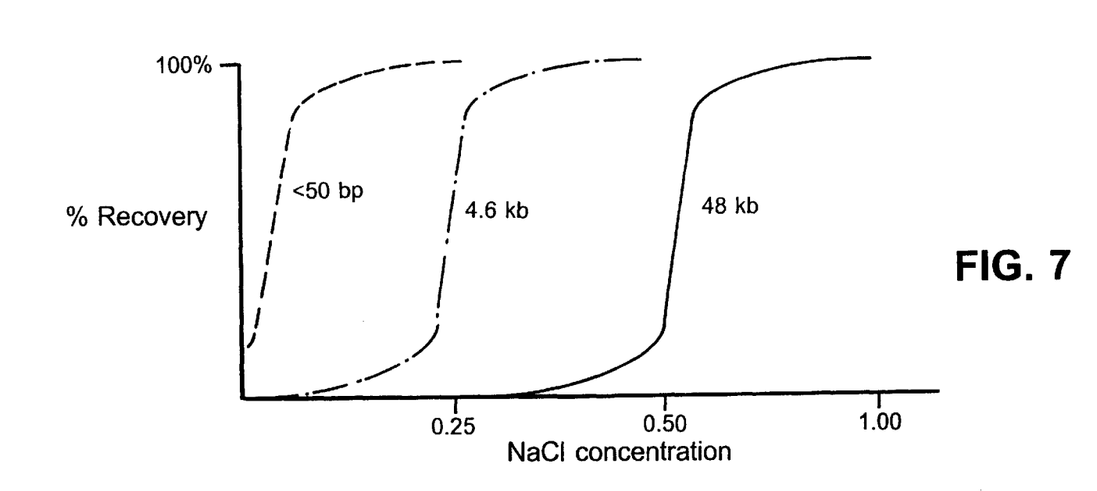
FIG. 7 is a graph of percent recovery of nucleic acids as a function of sodium chloride concentration at constant pressure for three sizes of DNA: 50 bp (•••), 4.6 kb (---), and 48.4 kb (—).

To test the effect of salt concentration for three different sized nucleic acids (i.e., 50 bp, 4.6 kb, and 48.4 kb), the pressure was held at 23,600 as the concentration of sodium chloride was increased from 0 to 1 M. The nucleic acids were detected as they eluted from the cartridge. The results are shown in the graph in FIG. 7. Most of the smallest nucleic acid, 50 bp, was eluted by 100 mM sodium chloride (i.e., as indicated by the dotted line). The 4.6 kb fragment was eluted at 250 mM, as shown by the dashed line. The solid line indicates that 500 mM sodium chloride was required to elute the largest nucleic acid, 48.4 kb. Thus, the nucleic acids can be separated on the basis of size by varying the salt concentration.

Figure 8:
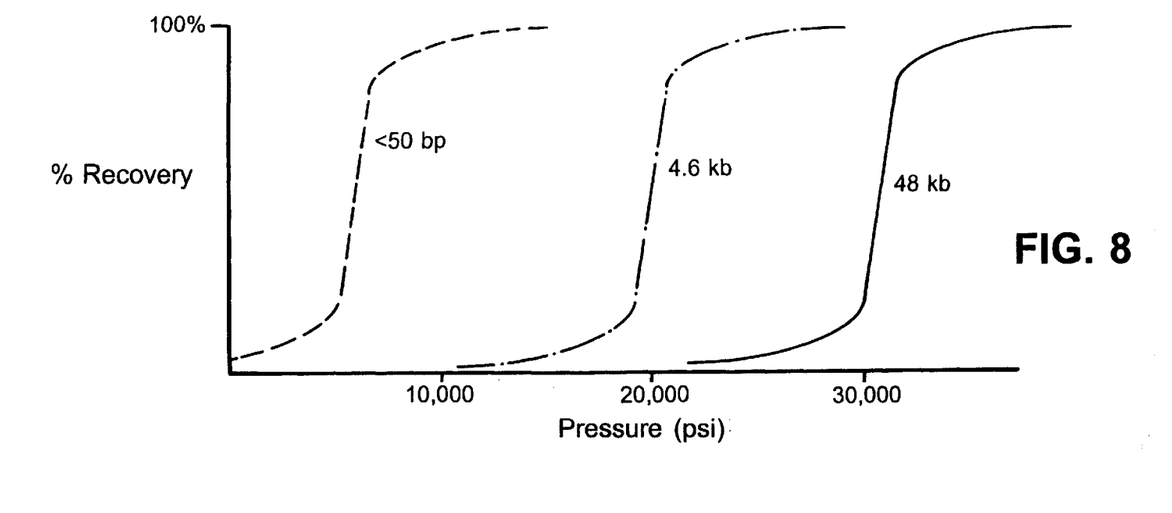
FIG. 8 is a graph of percent recovery of nucleic acids as a function of pressure at constant sodium chloride concentration for three sizes of DNA: 50 bp (•••), 4.6 kb (---), and 48.4 kb (—).

The effect of pressure was also studied, using the same three nucleic acid fragments. In this experiment, the sodium chloride concentration was held constant at 250 mM, as the pressure was increased from 14 to 40,000 psi. The nucleic acids were detected as they eluted from the cartridge. The results are shown in the graph in FIG. 8. Most of the smallest nucleic acid, 50 bp, was eluted at around 7,000 psi, as indicated by the dotted line. The 4.6 kb fragment was eluted at about 20,000 psi, as shown by the dashed line. The solid line indicates that approximately 32,000 psi was necessary to elute the largest nucleic acid, 48.4 kb. Thus, the nucleic acids can be separated on the basis of size by varying the elution pressure.

To test the specificity of the resin for nucleic acids, bovine serum albumin (BSA) was applied to the DEAE column. Serum albumins are multivalent and highly absorptive, and are the most abundant proteins in mammalian blood. It is therefore highly desirable that any DNA purification procedure for isolating DNA from blood be capable of separating BSA from DNA. Indeed, all of the protein was recovered in the flow through and MO washing solutions.

Agarose gels were used to check the integrity of DNA in the eluent solutions. Where sufficient DNA was recovered for analysis, the DNA molecules was found to be intact. In the remaining cases, there was not enough DNA to test on a gel. The DNA in the elution solutions was also quantified, using a dye specific for double-stranded DNA, PicoGreen (Molecular Probes, Eugene, Oreg.). The dye indicated that the majority of DNA (i.e., about 90%) was still double-stranded after applying pressure with a high concentration of salt.

EXAMPLE 2

Restriction Digestion of Eluate without Desalting pCMV-SV40T plasmid was isolated from a JM109 *E. coli* strain by alkaline lysis (Sambrook et al., *Molecular Cloning: A Laboratory Manual*, 2nd ed., Cold Spring Harbor Laboratory Press: Plainview, N.Y., 1989, pp. 1.25–1.26). 1.5 ml of an overnight bacterial culture was placed in a microcentrifuge tube and spun for 30 seconds at 12,000 g. The medium was removed and the cells were resuspended with vigorous vortexing in 100 μl of a solution containing 50 mM glucose, 25 mM Tris-HCl (pH 8.0), and 10 mM EDTA (pH 8.0). 200 μl of a freshly made solution of 0.2 N NaOH (containing 1% sodium dodecylsulfate, SDS) was added, and the tube was inverted five times. 150 μl of ice cold solution III (prepared by mixing 60 ml of 5 M potassium acetate, 11.5 ml of glacial acetic acid, and 28.5 ml of water) was added, then the sample was gently vortexed and incubated on ice for 4 minutes. The sample was centrifuged at 12,000 g for 5 minutes. The supernatant was transferred to a fresh tube and water was added to a final volume of 700 µl.

300 µl of the sample was purified using the Qiagen™ #12129 plasmid kit (Santa Clarita, Calif.) without the final isopropanol precipitation.

Another 300 µl of the sample was loaded onto a cartridge and processed as described in Example 1. The plasmid was eluted with 400 mM NaCl at 23,6000 psi.

45 µl of purified plasmid solution was mixed with 55 µl of buffer (containing 18 mM Tris-HCl pH 8.0, 18 mM $MgCl_2$, 1.8 mM dithiothreitol, and 180 µg/ml of BSA). A restriction digest reaction was initiated by adding 0.5 µl (40 units) of BamHI enzyme (Promega, Madison, Wis.) and incubated for 1 hour at 37° C.

The results were analyzed by agarose gel electrophoresis. The gel was stained using SYBR1 (Molecular Probes; Eugene, Oreg.). No digestion was seen with the Qiagen™ purified DNA, whereas the pressure eluted DNA showed two bands, indicating digestion of the plasmid at the two BamHI sites. This result demonstrated that, in contrast to a traditional nucleic acid elution procedure, DNA eluted under high pressure can be cleaved by a restriction enzyme without a precipitation or desalting step, other than a 1:1 dilution into reaction buffer.

EXAMPLE 3

Transfection of BSC 40 Cells with the BamHI Digestion Product

Purified pCMV-TAg (Campbell et al., Genes & Dev. 11:1098–1110, 1997) and purified pCMV control vector are each eluted from columns, collected, and assayed for transient expression of simian virus SV40 large TAg in a monkey kidney cell line, BSC 40. For transient transfection, 100 mM plates of ~50% confluent cells are transfected by the calcium phosphate procedure (Cherington et al., PNAS, 83:4307–4311, 1986). In the calcium phosphate procedure, 5.0 µg of the collected DNA is added to 1.0 ml of transfection solution referred to as HBS buffer (containing 137 mM sodium chloride, 0.37 mg/ml potassium chloride, 0.188 mg/ml dibasic sodium phosphate heptahydrate, 1.0 mg/ml dextrose, and 5 mg/ml HEPES). For optimum transfection efficiency, the pH of the HBS buffer is maintained at 7.05.

127 µl of 1 M calcium chloride is added dropwise to the 1.0 ml of HBS buffer containing the pCMV-TAg vector. The resulting DNA-calcium phosphate precipitate is added to the culture medium and left in contact with the cells for 4 hours. Upon removal of the precipitate, a 7 minute glycerol shock treatment is carried out, the cells are washed once with serum free DMEM, 10 ml of fresh complete medium was added, and the samples were assayed for protein expression 40–48 hours later.

The transfected cells are washed twice with ice cold PBS and lysed for 15 minutes in 1.0 ml Nonidet P-40 (NP40) lysis buffer (1% NP40, 10% glycerol, 137 mM sodium chloride, 5 mM EDTA, 20 mM Tris, pH 8.0) containing 5 mM sodium fluoride, 1 mM sodium orthovanadate, 25 mM β-glycerophosphate, and 10 µg of each of the following protease inhibitors: aprotinin, pepstatin, and leupeptin. The cell lysates are scraped from the dishes, centrifuged at 13,000 g, and the protein concentration is determined by Bradford assay (Biorad).

25–50 µg of total protein is boiled in sample buffer, and analyzed by SDS-polyacrylamide gel electrophoresis in 7.5% polyacrylamide gels. The proteins are transferred to Bioblot-nitrocellulose membranes (Costar, Cambridge, Mass.) and immunoblotting is performed by standard procedures (Towbin et al., PNAS, 76:4350–4354, 1979). The membranes are blocked for 30 minutes with 5% nonfat dry milk in PBS, prior to incubation with a monoclonal antibody specific to SV40 TAg (PAb101). Detection of SV40 TAg is carried out with horseradish peroxidase-conjugated secondary anti-mouse antibody (Jackson ImmunoResearch). Immunoblots were developed using enhanced chemiluminescence (ECL; Amersham, Arlington Heights, Ill.) and visualized on Kodak XAR film. Visualization of the film indicates SV40 TAg protein expression in cells transfected with pCMV-TAg as compared with expression in cells expressing the pCMV control vector.

EXAMPLE 4

Total RNA purification from BSC 40 Cells

BSC 40 monkey kidney cells that stably express SV40 large T antigen were grown to a density of $\sim 5 \times 10^6$ by the method of Chomczynski et al. (Anal. Biochem., 162:156–159, 1987). 1 ml RNA STAT-60™ (Tel-test, Inc., Friendswood, Tex.) was added directly to the cells. After incubating at room temperature for 5 minutes, the cells were scraped from the plate, homogenized by pipetting, and transferred to a sterile microcentrifuge tube. After addition of 0.2 ml chloroform, the solution was mixed vigorously for 15 seconds and the upper aqueous phase was separated by centrifugation. Following precipitation of the RNA with isopropanol, the RNA was pelleted by centrifugation in a microcentrifuge, and resuspended in 50 µl of sterile RNAse-free water. 10 µl of the RNA sample was then mixed with 500 µl of equilibration buffer (containing 750 mM sodium chloride; 50 mM MOPS, pH 7.0; 15% ethanol; and 0.15% Triton X-100).

Qiagen DEAE anion-exchange resin was packed in the "half-column" as described in Example 1, and washed with 1 ml equilibration buffer. 300 µl RNA sample was injected onto the DEAE column over 3 minutes. Then, 1 ml MO buffer (containing 1 M NaCl; 50 mM MOPS, pH 7.0; 15% ethanol) and 200 µl elution buffer (containing 250 mM sodium chloride and 50 mM Tris, pH 8.5) was applied to wash the column. Four consecutive 100 µl and three 300 µl elution fractions were collected at 23,600 psi. After taking the DEAE column out of the pressure flow apparatus, the column was washed with 1 ml of high salt buffer (containing 1.25 M sodium chloride; 50 mM Tris-HCl, pH 8.5; and 15% ethanol).

RNA in the collected samples was quantified using OliGreen DNA binding dye. To reduce background signals, RNA assay solutions were diluted 125-fold with TE buffer (containing 10 mM Tris-HCl and 1 mM EDTA, pH 7.5), which contained 1200-fold diluted OliGreen. Fluorescence emission intensity ($\lambda_{ex}$=485 nm, $\lambda_{em}$=580 nm) was measured with a FLUOROCOUNT™ microplate fluorometer (Packard Instrument Company, Meriden, Conn.), without background subtractions. The quantity of RNA was estimated by comparing the measured intensity with calibration curves obtained from known λDNA concentrations. The recovery of RNA in the elution fractions was calculated by dividing total RNA in the elution fractions by the total RNA bound in the column.

It was found that at 23,600 psi, more than 60% of RNA was released from the DEAE resin in the first 4 fractions.

The other three fractions contained about 40%; thus 100% recovery was achieved. The high salt wash solution was analyzed to verify this result; indeed, no RNA was detected in the subsequent high salt wash solutions. A 0.8% agarose gel was used to determine the integrity and purity of the RNA product in the collected samples. No degradation of the 28S and 18S rRNA was observed when compared to the control. The estimated yield of RNA, based on the gel electrophoresis, was consistent with the estimation made by fluorescence assay.

EXAMPLE 5

Purification of Messenger RNA (mRNA) from a Eukaryotic Sample

Two cartridges containing a solid phase are arranged in serial order, such that eluent from the first cartridge enters the second cartridge. The first cartridge is packed with an acidic DEAE activated anion exchange resin and the second is packed with a resin containing covalently linked polythymidine (poly-dT) resin.

An mRNA standard (positive control) is purified by standard methods using the POLY(A)PURE™ Kit (Ambion, Austin, Tex.). A salt concentration is found at which poly-dA mRNA is poorly bound at atmospheric pressure, but is more tightly bound at high pressure. Samples are loaded onto the cartridge containing the poly-dT resin, in a buffer containing 100 mM NaCl and 10 mM Tris-HCl, pH 7.2, at atmospheric pressure. The samples are then eluted with 300 µl of buffer containing 10 mM Tris-HCl (pH 8.0) and NaCl concentrations of 0 to 100 mM in increments of 2 mM. The salt is removed from the sample by washing twice in 10 mM Tris-HCl (pH 8.0) using a Centricon-100™ spin-filter (Millipore). The experiment is repeated at 25,000 psi for each sample. A buffer which gives poor binding at atmospheric pressure, but improved binding at high pressure is selected and referred to as "solution A."

A mammalian tissue sample is lysed by standard procedures (Chomczynski et al., supra) and total RNA is isolated on the DEAE column as described in Example 4. The cell debris is removed by centrifugation. The sample is applied to the double anion-exchange/poly-dT column. The column is washed with 300 µl of solution A. The column is then washed at 25,000 psi with 300 µl of solution A, thereby transferring the mRNA from the anion-exchange resin to the poly-da resin. The pressure is then lowered to atmospheric pressure and the resin is washed with 300 µl of either solution A or distilled water to recover the mRNA. The sample is analyzed for purity by agarose gel electrophoresis, UV spectroscopy, and a protein binding dye assay.

EXAMPLE 6

DNA Sequence Analysis to Detect p53 Mutations in Human Malignancies

Total RNA obtained from tumor samples is prepared by the method of Chomczynski et al. (supra) and collected from the DEAE column as in Example 4. Poly-A⁺RNA is subsequently isolated using oligo-dT cellulose (Ambion, Austin, Tex.). The gene of interest (i.e., p53) is amplified by reverse transcriptase-polymerase chain reaction (RT-PCR) (Promega, Madison, Wis.). The resulting cDNA is then analyzed for mutations by sequencing with the dideoxy chain termination method using a Sequenase 2.0 kit (United States Biochemicals), then compared with consensus mutations.

EXAMPLE 7

Isolation of RNA from Human Whole Blood

Total RNA is extracted by the method of Chomczynski (*Biotechniques*, 15:532–536, 1993). 300 µl of whole blood is mixed with 1.0 ml of red blood cell lysis solution (RBCS; containing 40 mM ammonium chloride, 10 mM potassium hydroxide, 7.5 mM potassium acetate, 2.5 mM sodium bicarbonate, 0.125 mM EDTA, and 0.1% glacial acetic acid). After 10 minutes at 4° C., the residual red blood cells and hemoglobin are pelleted by centrifugation (30 seconds at 12,000 g). An additional 1.0 ml RBCS is added to the pellet and mixed thoroughly. The centrifugation step described above is repeated. The supernatant is removed and the leukocyte pellet is resuspended in 350 µl leukocyte lysis solution (LLS; containing 4 M guanidinium isothiocyanate, 0.1 M β-mercaptoethanol, 10 mM sodium citrate pH 7.0, 0.5 M lauryl sarcosine, and 2.0% Triton-X100). The tube is vortexed vigorously prior to addition of 350 µl of 64% ethanol.

Following gentle inversion of the tube 5 to 7 times, 300 µl of the mixture is loaded onto a Qiagen DEAE anion-exchange column over 3 minutes, and the column is subsequently washed. RNA is eluted as described in Example 4, and collected in consecutive fractions, precipitated with isopropanol, and resuspended in 30 µl of RNAse-free water. The quality and integrity of total RNA eluted from the column is analyzed on a native 1.0% agarose gel stained with ethidium bromide. 5 µl of total RNA isolated from the column is sufficient for analyzing p53 mutations following RT-PCR with RETROSCRIPT™ and the p53 cDNA screening module with SUPERTAQ™ (Ambion, Austin, Tex.).

EXAMPLE 8

Isolation of Viral RNA from Human Whole Blood

Following elution of total RNA by the procedure of Example 7, 5 µl of RNA is amplified by RT-PCR using RETROSCRIPT™ (Ambion, Austin, Tex.). Primers specific to the viral genes of HIV are used for subsequent PCR amplification. The PCR products are then assayed by traditional DNA sequencing methods or Southern blot analysis. This procedure is repeated using primers specific for other viruses, including hepatitis A and hepatitis C.

Other Embodiments

From the description above, one skilled in the art can ascertain the essential characteristics of the invention and without departing from the spirit and scope thereof, can make various changes and modifications of the invention to adapt it to various usages and conditions.

It is to be understood that while the invention has been described in conjunction with the detailed description thereof, that the foregoing description is intended to illustrate and not to limit the scope of the appended claims. Other aspects, advantages, and modifications are within the scope of the following claims.

For example, cartridges containing multiple, layered resins are also within the scope of the claims. A layer of cation-exchange resin, for instance, will capture any positively charged proteins which might bind to the DNA. Hydrophobic (e.g., reverse-phase) resins can bind to the lipids in the sample.

What is claimed is:

1. A device for insertion into a pressure-modulation apparatus, said device comprising:
   an electrode array system arranged along two axes;
   tubes interconnecting said electrodes along the axes, wherein said tubes contain a solid phase; and
   electrical terminals that contact a current source in the pressure modulation apparatus.

2. The device of claim 1, wherein said tubes are electrophoretic capillaries.

3. The device of claim 1, wherein said tubes are electroosmotic capillaries.

4. The device of claim 1, wherein said electrode array system is configured on a microchip.

5. The device of claim 1, wherein said solid phase comprises hydroxyapatite.

6. The device of claim 1, wherein said solid phase comprises oligo-dT.

7. The device of claim 1, wherein said solid phase comprises silica gel.

8. The device of claim 1, wherein said solid phase comprises an anion-exchange resin.

9. The device of claim 1, wherein said solid phase comprises microfabricated silicon.

10. A cartridge for insertion into a high pressure apparatus, said cartridge comprising:
    a column adapted to fit into said high pressure apparatus; and
    a solid phase packed in said column.

11. The cartridge of claim 10, wherein said column has a capacity of 10 $\mu$l to 5 ml.

12. The cartridge of claim 10, wherein said column has a capacity of 10 $\mu$l to 1 ml.

13. The cartridge of claim 10, wherein said solid phase comprises hydroxyapatite.

14. The cartridge of claim 10, wherein said solid phase comprises oligo-dT.

15. The cartridge of claim 10, wherein said solid phase comprises silica gel.

16. The cartridge of claim 10, wherein said solid phase comprises an anion-exchange resin.

17. The cartridge of claim 10, wherein said solid phase comprises microfabricated silicon.

* * * * *

UNITED STATES PATENT AND TRADEMARK OFFICE
CERTIFICATE OF CORRECTION

PATENT NO.   : 6,111,096
DATED        : August 29, 2000
INVENTOR(S)  : James A. Lougharn, Jr., Robert A. Hess and Feng Tao It is certified that error appears in the above-identified patent and that said Letters Patent is hereby corrected as shown below:

Please insert the following references on title page:

-- U.S. Patent Documents

| | | | | |
|---|---|---|---|---|
| 5707812 | 01/13/98 | Horn et al. | 435 | 6 |
| 5650506 | 07/22/97 | Woodard et al. | 536 | 25.4 |
| 5637687 | 06/10/97 | Wiggins | 536 | 25.4 |
| 5596092 | 01/21/97 | Schneider | 536 | 25.4 |
| 5700639 | 12/23/97 | Trauth et al. | 435 | 6 |
| 5606046 | 02/25/97 | Woodard et al. | 536 | 25.4 |
| 5610291 | 03/11/97 | Woodard et al. | 536 | 25.4 |
| 5610290 | 03/11/97 | Woodard et al. | 536 | 25.4 |
| 5616701 | 04/01/97 | Woodard et al. | 536 | 25.4 |
| 5605839 | 02/25/97 | Simpson et al. | 436 | 89 |
| 5346999 | 09/13/94 | Cathcart et al. | 536 | 25.41 |
| 4323439 | 04/06/82 | O'Farrell | 204 | 180 |

Foreign Patent or Published Foreign Patent Application
0 127 327           12/05/84           EPO
WO97/31105          08/28/97           PCT Other Documents (Including Author, Title, Date, Place of Publication)

Bollag, Daniel M., "Protein Extraction and Solubilization", *Protein Methods*, 2nd ed., pp. 27-49, 1996

Madou, Marc I., "Fluid Propulsion Mechanisms" and "Thermal Actuators", *Fundamentals of Microfabrication*, pp.431-434, 439-441, 446-447, 1997

"Mini-Bomb Cell Disruption Chamber" and "Ultrasonicators", *KONTES*, Catalog, pp.46, 356, 1992

Carter, M.J. et al., "An Inexpensive and Simple Method for DNA Purifications on Silica Particles", Nucleic Acids Research, Vol. 21, No. 4, p. 1044, 1993

UNITED STATES PATENT AND TRADEMARK OFFICE
CERTIFICATE OF CORRECTION

PATENT NO. : 6,111,096
DATED : August 29, 2000
INVENTOR(S) : James A. Laugharn Jr., Robert A. Hess and Feng Tao It is certified that error appears in the above-identified patent and that said Letters Patent is hereby corrected as shown below:

"Isolation of RNA from Plant Cell Suspension Cultures and Calli by Sonication", *BioTechniques*, Vol. 23, No. 6, pp. 996-1000, 1997

Wages, Jr., J.M. et al., "Affinity Purification of RNA: Sequence-Specific Capture by Noionic Morpholino Probes", *BioTechniques*, Vol. 23, No. 6, pp. 1116-1121, 1997

Boyle, J.S., et al., "An Inexpensive Alternative to Glassmilk for DNA Purification", *Trans*. Genet., 11 (1):8, 1995 --

Signed and Sealed this

Twenty-third Day of October, 2001

*Attest:*

*Attesting Officer*

NICHOLAS P. GODICI
*Acting Director of the United States Patent and Trademark Office*